(12) United States Patent
Park et al.

(10) Patent No.: US 8,673,633 B2
(45) Date of Patent: Mar. 18, 2014

(54) METHOD FOR PRODUCING INDUCED PLURIPOTENT STEM CELLS WITH HIGH EFFICIENCY AND INDUCED POLURIPOTENT STEM CELLS PROUCED THEREBY

(75) Inventors: Young-Bae Park, Seoul (KR); Hyo-Soo Kim, Seoul (KR); Yoo-Wook Kwon, Seoul (KR); Hyun-Jai Cho, Seoul (KR); Jae-Seung Paek, Gunpo-si (KR)

(73) Assignee: Seoul National University Hospital, Seoul (KR)

( * ) Notice: Subject to any disclaimer, the term of this patent is extended or adjusted under 35 U.S.C. 154(b) by 273 days.

(21) Appl. No.: 13/120,331

(22) PCT Filed: Sep. 17, 2010

(86) PCT No.: PCT/KR2010/006374
§ 371 (c)(1),
(2), (4) Date: Mar. 22, 2011

(87) PCT Pub. No.: WO2011/037367
PCT Pub. Date: Mar. 31, 2011

(65) Prior Publication Data
US 2011/0256626 A1    Oct. 20, 2011

(30) Foreign Application Priority Data

Sep. 22, 2009  (KR) .................. 10-2009-0089330
Jan. 8, 2010   (KR) .................. 10-2010-0001940

(51) Int. Cl.
*C12N 5/00*   (2006.01)
*C12N 5/02*   (2006.01)
*C12N 15/00*  (2006.01)

(52) U.S. Cl.
USPC .......................................... 435/325; 435/455

(58) Field of Classification Search
USPC ................................. 435/325, 455
See application file for complete search history.

(56) References Cited

U.S. PATENT DOCUMENTS

| | | | |
|---|---|---|---|
| 6,875,607 B1 * | 4/2005 | Reubinoff et al. | 435/325 |
| 6,921,632 B2 * | 7/2005 | Lim et al. | 435/1.1 |
| 8,298,825 B1 * | 10/2012 | Hochedlinger et al. | 435/377 |
| 2003/0131370 A1 * | 7/2003 | Allen et al. | 800/18 |

FOREIGN PATENT DOCUMENTS

| KR | 10-2009-0130582 A | 12/2009 |
|---|---|---|
| WO | 2011-037301 A1 | 3/2011 |

OTHER PUBLICATIONS

Moore (2002, DNA and Cell Biol., vol. 21(5/6), pp. 443-451).*
Thomson (1995, PNAS, vol. 92, pp. 7844-7848).*
NIH (Stem Cells: Scientific Progress and Future Research Directions, Department of Health and Human Services, Chapter 1, p. 14, Jun. 2001).*
NIH (Stem Cells: Scientific Progress and Future Research Directions, Department of Health and Human Services, Chapter 3, p. 14, Jun. 2001).*
Takahashi (Cell, 2006, vol. 126:663-676).*
Takahashi (Cell, 2007, vol. 131: 861-872).*
Okita (Nature, Jul. 19, 2007, vol. 448, p. 313-317).*
Wernig (Nature, Jul. 19, 2007, vol. 448, p. 318-324).*
Yu (Science, 2007, vol. 318, p. 1917-1920).*
Meissner (Nature, 2006, vol. 439, p. 212-215).*
Hanna (Science, 2007, vol. 318, p. 1920-1923).*
Meissner (Nature Biotechnology, 2007, vol. 25: 1177-1181).*
Blelloch (Cell Stem Cell, Sep. 13, 2007, vol. 1, p. 245-247).*
Aoi (Science, Aug. 2008, vol. 321, p. 699-702; published online Feb. 14, 2008).*
Nakagawa (Nat Biotechnol, 2008, vol. 26: 101-106; published online Nov. 11, 2007).*
Wernig (Cell Stem Cell, Jan. 2008, vol. 2:10-12).*
Stadtfeld (Cell Stem Cell, Mar. 6, 2008, vol. 2, p. 230-240; published online Feb. 14, 2008).*
Kim (Cell, Feb. 6, 2009, vol. 136, p. 411-419).*
Stadtfeld (Genes & Develop. 2010, vol. 24, p. 2239-2263).*
Patel (Stem Cell Rev. Sep. 2010, vol. 6, No. 3, p. 367-380).*
Rajasingh (Circulation Res., May 15, 2008, vol. 102, e107-e117).*
Bru (Exp. Cell Res. Aug. 15, 2008, vol. 314, No. 14, p. 2634-2642).*
Rajasingh, J., et al., "Cell-free embryonic stem cell extract mediated derivation of multipotent stem cells from NIH3T3 fibroblasts for functional and anatomical ischemic tissue repair", Circulation Research, vol. 102, pp. eI07-eI1117, May 15, 2008, See abstract, figures 1-8.
Bru, T., et al., "Rapid induction of pluripotency genes after exposure human somatic cells to mouse ES cell extracts" Experimental Cell Research, vol. 314, pp. 2634-2642, May 29, 2008, See abstract, figures 1-6.

* cited by examiner

*Primary Examiner* — Michael C. Wilson
(74) *Attorney, Agent, or Firm* — Lucas & Mercanti, LLP

(57) ABSTRACT

The present invention provides a method for producing customized pluripotent stem cells. Specifically, the present invention comprises following steps: extracting proteins from any of the dedifferentiated stem cells or induced pluripotent stem cells, the said dedifferentiated or pluripotent stem cells being prepared by any known method; introducing the protein extract into the adult somatic cells; and culturing the adult somatic cells to produce pluripotent stem cells having the same pluripotency as that of embryonic stem cells. In addition, pluripotent stem cells produced according to the present method and cell therapeutics comprising the same are provided. The method allows pluripotent stem cells to be produced very easily and at a significantly higher yield, compared to typical methods.

10 Claims, 8 Drawing Sheets a) Gene expression of pluripotent stem cells b) Expression of Pluripotency markers in ES or iPS cells a) Visulation of Teratoma formed 4 weeks after injection b) Ectoderm neuroepithelium    osteoid-bone    neuroglial tissue c) Mesoderm Glandular epithelium    cartilage    muscle d) Endoderm ciliate columnar epithelium    exocrine pancreas    squamous epithelium D6Mit102-Genomic DNA PCR M: marker, 1: C57 cFB, 2: FVB sFB, 3: C57 mES, 4: FVBsFB-iPS,
5: C57sFB-iPSe2, 6: FVBsFB-iPSe1

D6Mit285-Genomic DNA PCR

M: marker, 1: C57 cFB, 2: FVB sFB, 3: C57 mES, 4: FVBsFB-iPS,
5: C57sFB-iPSe2, 6: FVBsFB-iPSe1, M: marker a) C57 mES extract treated group b) FVB iPS extract treated group

C57 mouse skin fibroblast

Oct4-GFP skin fibroblast

METHOD FOR PRODUCING INDUCED PLURIPOTENT STEM CELLS WITH HIGH EFFICIENCY AND INDUCED POLURIPOTENT STEM CELLS PROUCED THEREBY

CROSS-REFERENCE TO RELATED APPLICATIONS

This application is a 371 of PCT/KR2010/006374 filed on Sep. 17, 2010, which claims the benefit of Korean Application Nos. 10-2009-0089330 filed on Sep. 22, 2009, and 10-2010-0001940 filed on Jan. 8, 2010, the contents of each of which are incorporated herein by reference.

FIELD OF THE INVENTION

The present invention relates to a method for the production of customized pluripotent stem cells by infusing adult somatic cells with a protein extract from all of the dedifferentiated stem cells or induced pluripotent stem cells, which may be prepared by any known methods. In addition, the present invention relates to the pluripotent stem cells produced by the method of the present invention. Furthermore, the present invention is concerned with cell therapeutics comprising the pluripotent stem cells.

BACKGROUND OF THE INVENTION

A stem cell is a generic name for an undifferentiated type of cells found in tissues of embryos, fetuses and adults, which are characterized by the ability to differentiate into a diverse range of specialized cell types. Stem cells may be classified according to various criteria. One of the most frequently used criteria is a source from which stem cells are derived. The two broad types of mammalian stem cells are: embryonic stem cells (ES cells) that are isolated from the inner cell mass of blastocysts, and adult stem cells that are isolated from adult somatic cells. Potency allows the classification of stem cells: pluripotent stem cells, multipotent stem cells, and unipotent stem cells. Pluripotent stem cells can differentiate into cells derived from any of the three germ layers. Embryonic stem cells are representative of pluripotent stem cells. Adult stem cells show multipotency or unipotency.

ES cells are pluripotent stem cells with the potency to differentiate into cells of all tissues constituting the body. However, the preparation of ES cells results in destruction of the fertilized human embryo, which raises ethical issues. In addition, derivation from limited oocytes is an obstacle regarding the use of ES cells in the development of cell therapeutics due to the lack of immune compatibility, which gives rise to transplant rejection. To avoid these problems, a variety of alternatives have been developed for reprogramming adult somatic cells into pluripotent stem cells mimicking embryonic stem cells.

Representative among them are adult somatic cells nuclear transfer (SCNT), fusion with ES cells, and reprogramming by defined factors. SCNT requires a large amount of oocytes due to the very low efficiency thereof. Fusion with ES cells is problematic in terms of stability because the pluripotent cells induced thereby contain two additional pairs of genes. Characterized by the induction of reprogramming with defined genes, the reprogramming by defined factors, which employs a viral delivery system containing a potent oncogene may cause tumorigenicity. Further, low efficiency and methodological difficulty leads to a significant problem in the practical availability of the reprogramming by defined factors in the development of cell therapeutics.

SUMMARY OF THE INVENTION

It is an object of the present invention to provide a method for producing customized, pluripotent stem cells suitable for use in cell therapy, at high efficiency with safety and stability, which can give a solution to the ethical problem of destroying embryos.

In order to accomplish the object, differentiated adult somatic cells are reprogrammed to dedifferentiate into stem cells by infusing a protein extract from iPS into the adult somatic cells.

As mentioned above, the method of the present invention can avoid the ethical problem of embryo destruction because it employs no embryonic stem cells and can allow the generation of safe pluripotent stem cells free of oncogenesis because it does not employ an oncogen-carrying virus. Also, the iPS protein extract according to the present invention enables pluripotent stem cells to be generated very easily and at significantly higher yield than do conventional methods, greatly contributing to the commercialization of cell therapy. In addition, originating from adult somatic cells, the induced pluipotent cells of the present invention are useful for the development of immunocompatible cell therapeutics customized for individuals. Accordingly the present invention can greatly contribute the treatment of various incurable diseases such as cardiovascular diseases, nerve system diseases, diabetes, etc. Further, the method can be used in the production of cloned animals while maintaining high level of safety and efficiency.

DETAILED DESCRIPTION OF THE INVENTION

Figure 1:
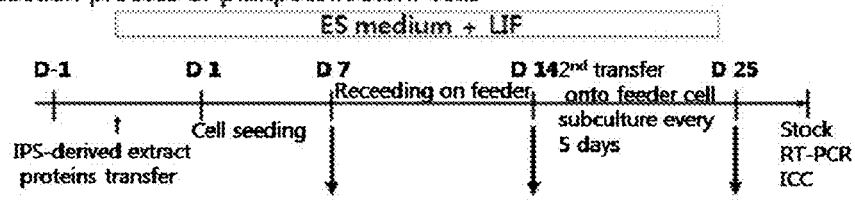
FIG. 1 shows the induction of pluripotent stem cells having the same pluripotency as embryonic stem cells by infusing adult somatic cells with an iPS protein extract in a schematic view of the overall procedure (a), induced pluripotent stem cells (b, c), embryonic stem cells and iPS used for protein extract as controls (d), and alkaline phosphatase staining results of embryonic stem cells and induced pluripotent stem cells (e).
Figure 1:
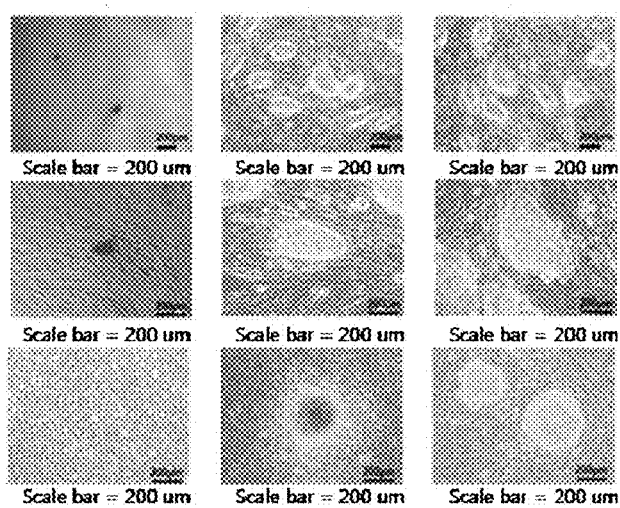
Figure 1:
Figure 1:
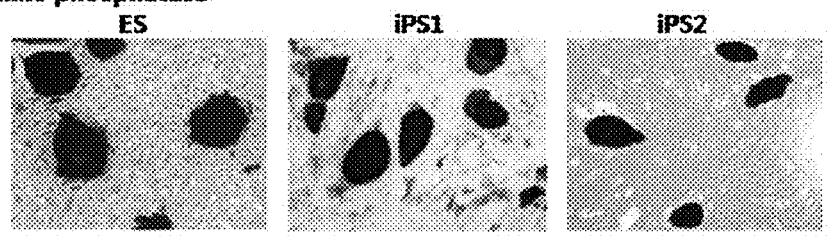

The present invention pertains to a method for the preparation of customized pluripotent stem cells having the same pluripotency as that of embryonic stem cells, comprising extracting proteins from all types of dedifferentiated stem cells or iPS; introducing the extract into adult somatic cells; and culturing the adult somatic cells to induce the pluripotent stem cells.

The term "embryonic stem cell", as used herein, refers to a cell with pluripotency, which is derived from the inner cell mass of the blastocyst, an early-stage embryo. The term "adult somatic cell," as used herein, refers to any cell forming the body of an organism after birth, as opposed to the embryonic stem cell. As used herein, the term "pluripotent stem cell" refers to a stem cell capable of differentiating into all cells, i.e. cells derived from any of the three germ layers, that is, endoderm, mesoderm and ectoderm. Embryonic stem cells are representative of pluripotent stem cells. As used herein, the term "dedifferentiated stem cell or induced pluripotent stem cell (iPS)" refers to a type of pluripotent stem cell artificially derived from a non-pluripotent, adult somatic cells, by compulsory dedifferentiation (reprogramming). The term "customized pluripotent stem cell", as used herein, is intended to refer to a pluripotent stem cell genetically consistent with a donor cell (adult somatic cells), meaning that the pluripotent stem cell is derived from the donor cell (adult somatic cells). The term "differentiation," as used herein, refers to a process by which during the division, proliferation and growth thereof; a cell becomes specialized in structure and function, that is, a cell changes its morphology or function changes so as to perform a given work. As used herein, the term "cell therapeutics" is intended to refer to a medicine, prepared by isolating, culturing and specially manipulating human cells or tissues, for use in the treatment, diagnosis and prevention of a disease, that is, a medicine, prepared by a series of processes of proliferating and selecting autologuous or heterologuous cells in vitro or changing biological properties of cells to rehabilitate the function of cells or tissues, for use in the treatment, diagnosis and prevention of a disease. According to the degree of differentiation, cell therapeutics may be classified into adult somatic cells therapeutics and stem cell therapeutics. The present invention is directed toward stem cell therapeutics.

The present invention provides a method for the production of pluripotent stem cells from nearly all adult somatic cells having various genetic backgrounds. No limitations are imparted to the genetic backgrounds of the adult somatic cells used in the present invention. For example, skin fibroblasts (sFB) and cardiac fibroblasts (cFB) derived from C-57 BL6 and FVB mice may be used.

In the method of the present invention, iPS is cultured to yield an extract. All kinds of iPS, prepared using various methods including reprogramming by the four factors Oct4, Sox2, Klf4, and c-Myc may be used in the present invention. For example, the iPS cells which are reprogrammed with a protein extract from mouse embryonic stem cell can be used. In detail, iPS under culture is treated with a protease and the resulting extracts are pooled, followed by preparing iPS-derived extract proteins. In this context, the extraction technique may be a conventional technique for producing a high concentration of protein extracts as will be described in detail in the following example section. When the production efficiency of the customized pluripotent stem cells is taken into consideration, the protein extract is used preferably at a concentration of from 10 to 50 mg/ml and more preferably at a concentration of from 20 to 30 mg/ml. At a concentration outside the range, the induction efficiency decreases significantly.

In the method of the present invention, the iPS-derived protein extract is introduced into adult somatic cells. In this context, adult somatic cells are permeabilized by treatment with a membrane permeabilizing enzyme, followed by the introduction of the iPS extract. In an embodiment, streptolysin O may be used as a membrane permeabilizing enzyme.

In the method of the present invention, the iPS extract-introduced adult somatic cells are cultured and induced to customized pluripotent cells. An embryonic stem cell medium may be used to culture the extract-induced adult somatic cells. In detail, immediately after the introduction of the extract into adult somatic cells, the medium is changed with an embryonic stem cell medium to culture the cells. An embryonic stem cell medium useful in the present invention may be a DMEM (Dulbecco's Modified Eagle Medium) supplemented with 10% FBS (Fetal Bovine Serum), 0.1 mM MEM (Minimum Essential Medium), nonessential amino acid, 0.1 mM β-mercaptoethanol, 100 U/ml penicillin, 100 µg/ml streptomycin, and 20 ng/ml LIF (Leukemia Inhibitory Factor). It is apparent to those skilled in the art that the concentrations of the compounds added to the DMEM may be changed within the range which guarantees the effect of the present invention.

The method of the present invention may further comprise additionally culturing the adult somatic cells on a feeder cell layer. In an embodiment of the present invention, the iPS extract is introduced into adult somatic cells which are then cultured for 7 days in an embryonic stem cell medium and transferred to and cultured for an additional 7 days on a feeder cell layer. On day 14, the cells are reseeded on a fresh feeder cell layer, followed by a passage every five days. STO cells may be used as feeder cells.

In accordance with another aspect, the present invention provides a method for the production of customized pluripotent stem cells, comprising preparing a protein extract at a concentration of from 20 to 30 mg/ml from iPS; introducing the extract into adult somatic cells; incubating the cells in an embryonic stem cell medium immediately after the introduction of the protein extract; and 7 days after the incubation, transferring and culturing the cells on a feeder cell layer.

The iPS reprogrammed from adult somatic cells according to the method of the present invention has the same differentiation potency as that of embryonic stem cells. In detail, the iPS of the present invention is indistinguishable from embryonic stem cells in terms of morphology (see FIGS. 1d and 1e). In addition, the iPS reprogrammed according to the present invention was found to express the genes Nanog, Oct4, Sox-2, and E-Ras and the proteins Oct4 and SSEA1, which are hallmarks of embryonic stem cells (FIG. 2).

Further, an experiment was performed to examine whether the iPS of the present invention had the same pluripotency as that of embryonic stem cells. When transplanted with the iPS, immune-deficient mice were observed to form teratoma that can differentiate into the endoderm, the mesoderm, and the ectoderm. (see FIG. 3)

Next, a tetraploid complementation assay was conducted to prove the in vivo pluripotency of the iPS reprogrammed according to the method of the present invention. By this assay, the characters of embryonic stem cells can be examined in vivo under the most stringent standards. The production of a tetraploid cell (4n) is done by taking an embryo (2n) at the two-cell stage and fusing the two cells by manipulation. In the tetraploid complementation assay, such a tetraploid embryo is combined with the iPS of the present invention.

Figure 4:
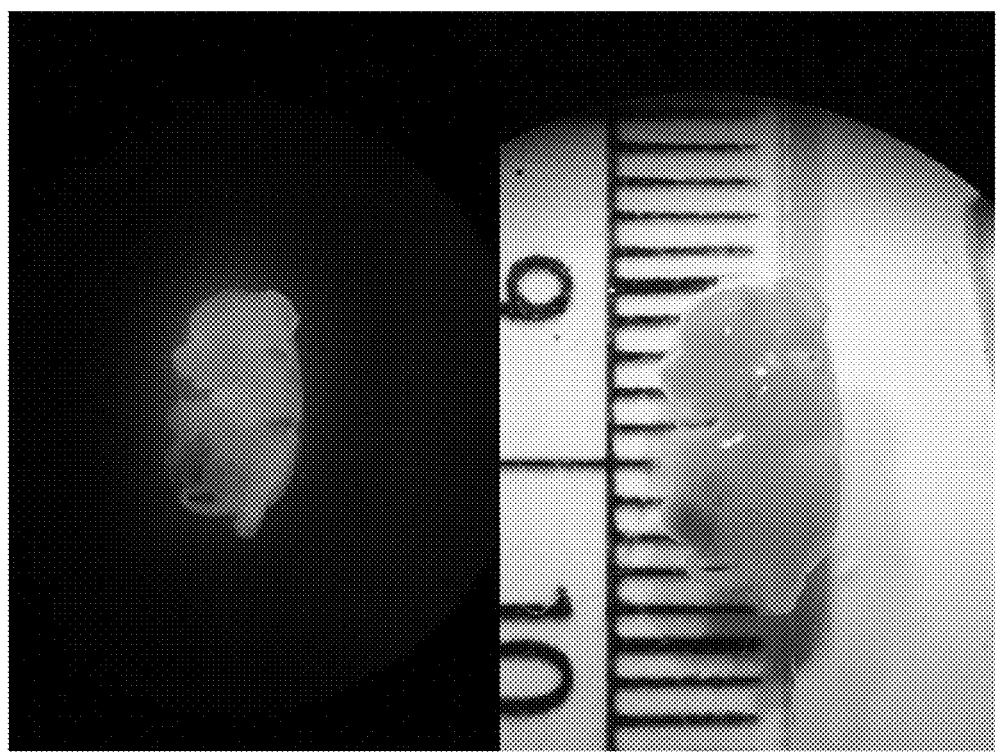
FIG. 4 shows a 12.5-day old embryo generated by tetraploid complementation to assay in vivo pluripotency of the induced pluripotent stem cells according to the present invention.

The embryo will then develop normally; the fetus is exclusively derived from the iPS cell, while the placenta is exclusively derived from the tetraploid cells. 12.5 days after implantation in the uterine wall of pseudopregnant female mice by a tetraploid complementation assay, an embryo was obtained as shown in FIG. 4, indicating that the iPS reprogrammed by the method of the present invention can be developed into an intact individual.

Figure 5:
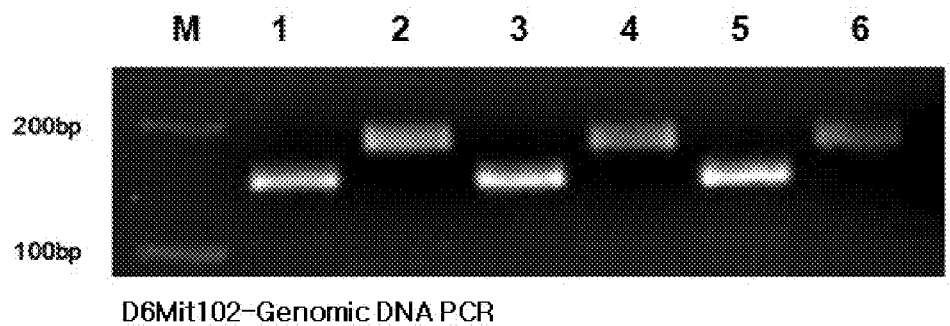
FIG. 5 shows results of the PCR conducted with specific MIT (microsatellite) markers to verify the origination of the induced pluripotent stem cells according to the present invention.
Figure 5:
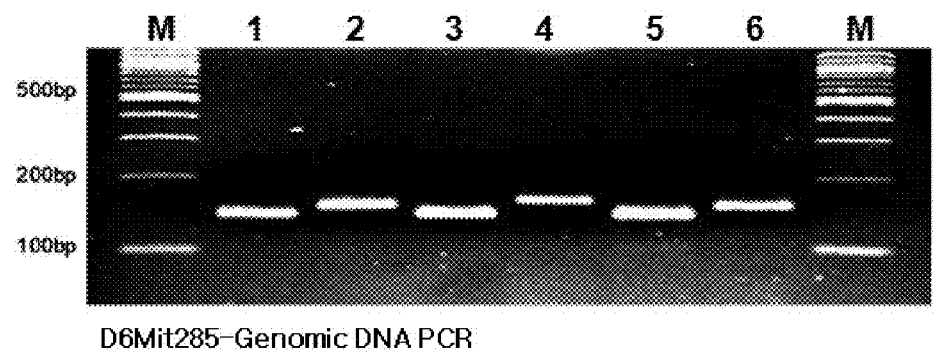

Next, PCR (polymerase chain reaction) were performed with unique MIT (microsatellite) markers on genomic DNA to examine whether the iPS originated from the protein donor iPS or the adult somatic cells. As a result, the induced pluripotent stem cells according to the present invention was proven to be customized pluripotent stem cells reprogrammed from adult somatic cells (FIG. 5).

Figure 6:
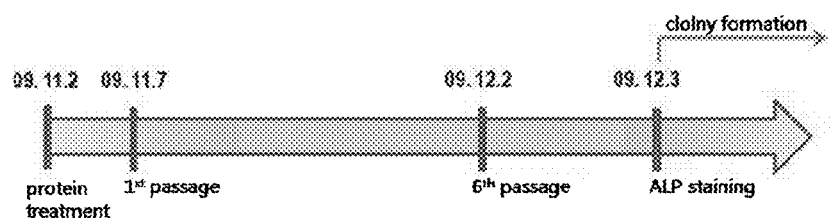
FIG. 6 shows the comparison of iPS production yield between an embryonic stem cell extract (a) and an iPS extract (b) in schematic views of colony formation procedure.
Figure 6:
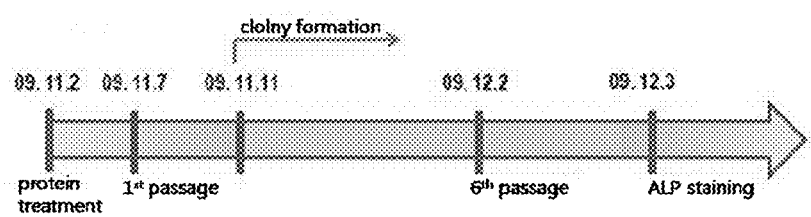

Further, a comparison was made in terms of reprogramming efficiency between iPS and ES protein extracts. As a result, the efficiency of reprogramming by an iPS protein extract was significantly improved as compared with an ES protein extract. In detail, the iPS protein extract allows the iPS to start to form colonies much earlier and guarantees a significantly greater rate of colony formation than does the ES protein (FIG. 6).

As described above, the induced pluripotent stem cells of the present invention have the same pluripotency as that of embryonic stem cells as well as the same genetic origin as that of the adult somatic cells used, and can be customized for individual patients in need thereof. Also, it is apparent that the method of the present invention produces the pluripotent stem cells at high efficiency as compared to conventional methods. Accordingly, the method for the preparation of iPS according to the present invention is anticipated to contribute to the commercialization of cell therapy with the customized iPS as well as the production of cloned animals including mammals.

In the following, the present invention is described in detail through experiments. The experiments are not intended to limit the technical spirit of the present invention, but are intended to describe the invention.

EXAMPLES

Example 1

Induction of Customized Pluripotent Stem Cell from Adult Somatic Cells (1) Preparation of iPS Extract Mouse fibroblast derived iPS (FVBsFB-iPS) generated with a C57 mouse embryonic stem cell (C57 mES) extract was harvested by treatment with 0.25% trypsin-EDTA for 3 min, washed with phosphate-buffered saline (PBS), and collected by centrifugation. The cell pellet thus obtained was resuspended in 1 mL of cold cell lysis buffer (100 mM HEPES, pH 8.2, 50 mM NaCl, 5 mM $MgCl_2$, 1 mM dithiothreitol, and protease inhibitor), and put on ice for 30~45 min, with vortexing once every five minutes. The cells were homogenized by 3~5 passages through a syringe equipped with a 20-gage needle, followed by centrifugation at 15,000 rpm at 4° C. for 30 min. The supernatant thus obtained was transferred to a new tube which was then stored at −80° C. until use. The protein concentration was found to range from 20 to 30 mg/ml.

(2) Permeabilization of Adult Somatic Cells Membrane

In the present invention, C57 BL6 mouse fibroblast cells (C57sFB) and FVB mouse skin fibroblast cells (FVBsFB) were used as adult somatic cells. The fibroblast cells were harvested with trypsin-EDTA, washed with cold PBS and collected by centrifugation. The cell pellet thus obtained was resuspended in a cold $Ca^{2+}$- and $Mg^{2+}$-free Hanks balanced salt solution (HBSS) (concentration of 100,000 cells/100 μL) and transferred to 1.5 mL tubes. After centrifugation at 120 g at 4° C. for 5 min in a swing-out rotor, the resulting cell pellet was resuspended in 97.7 μL of cold HBSS and incubated at 37° C. for 2 min in water bath. Streptolysin O (SLO) was diluted (1:10) in cold HBSS to a concentration of 100 g/mL. The SLO dilution was added in an amount of 2.3 μL to the reaction solution to form a final SLO concentration of 230 ng/mL Afterwards, the cell solution was incubated for 50 min in a 37° C. water bath during which it was turned upside down once every ten min. To this cell solution on ice was added 200 μL of HBSS, followed by centrifugation at 120 g at 4° C. for 5 min in a swing-out rotor to collect cells.

(3) Introduction of iPS Extract into Adult Somatic Cells

After the permeabilization, the adult somatic cells pellet was resuspended at a density of 1000 cells/μL in 200 μL of the iPS extract. To this suspension were added ATP-regeneration system (10 mM creatine phosphate and 25 g/mL creatine kinase) and 1 mM of each of deoxynucleotide triphosphates (dNTPs), followed by incubation for 1 hr in a 37° C. water bath with turning upside down once every ten minutes. To reseal plasma membranes, the cell suspension was diluted with 1 mL of an ESC medium containing 2 mM $CaCl_2$, and incubated for 2 hours in a 37° C. incubator. DMEM supplemented with 10% FBS, 0.1 mM MEM nonessential amino acid (Gibco BRL), 0.1 mM β-mercaptoethanol (Sigma), 100 U/mL penicillin (Sigma), 100 μg/mL streptomycin (Sigma), and 20 ng/mL recombinant leukemia inhibitory factor (LIF) was used as a medium for the embryonic stem cells. The cells were washed with PBS, pelletized by centrifugation, resuspended in the medium, and seeded at a population of 100,000 cells per 0.1% gelatin-coated dish.

(4) Induction of Customized Pluripotent Stem Cell by Culturing iPS Extract-Introduced Adult Somatic Cells The cells seeded on the dish were cultured at 37° C. in the same embryonic stem cell medium as in (3) in a 5% $CO_2$ incubator. The medium was changed with a fresh one for the first time after incubation for two days, and then every day. On the 7th day of culture, the cells were divided into two groups at a ratio of 1:2 per dish and cultured on a mitomycin C (MMC)-treated feeder cell layer. On the 14th day of culture (D14), the cells were transferred to a fresh feeder cell layer. STO cells were used as feeder cells. The medium was newly changed every day, with transfer to a new feeder cell layer at regular interval of five days.

Figure 2:
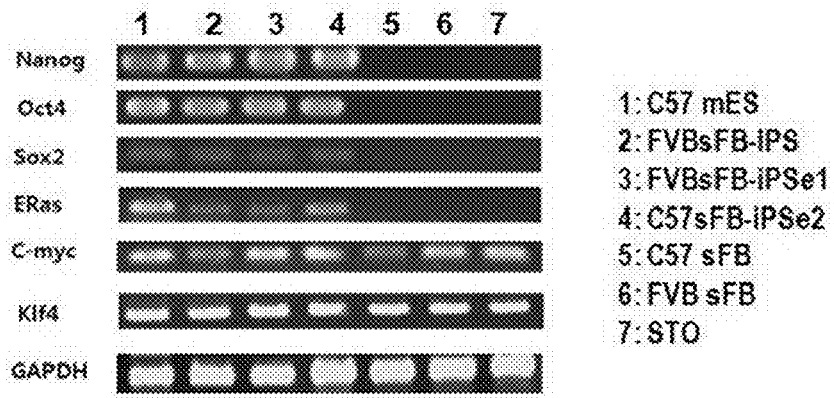
FIG. 2 shows gene expression patterns (a) and protein expression patterns (b) of the induced pluripotent stem cells according to the present invention.
Figure 2:
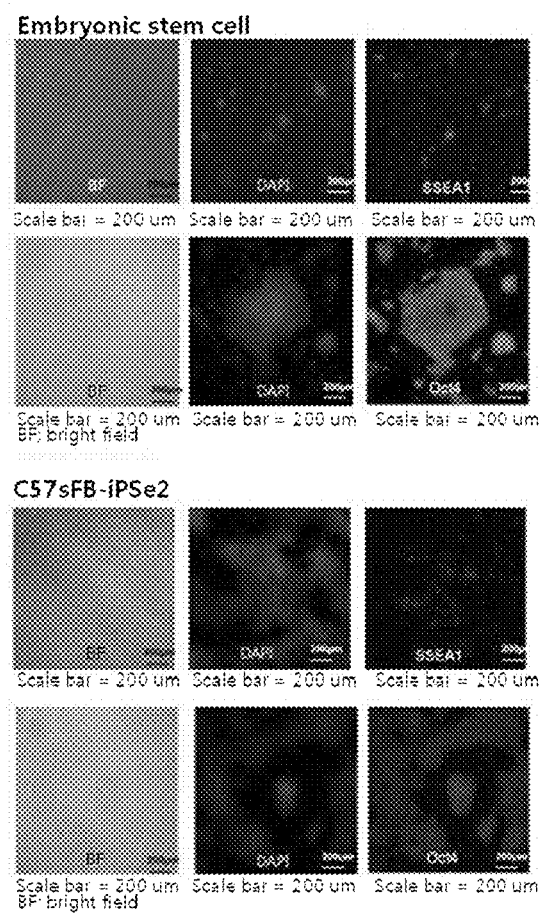

FIG. 1A is a schematic view showing the overall procedure of reprogramming customized pluripotent stem cells according to the method of present invention. The pluripotent stem cell 1 (FVBsFB-iPSe1) and 2 (C57sFB-iPSe2) reprogrammed according to the method of the present invention are given in FIGS. 1B and 1C, respectively. The pluripotent stem cells reprogrammed according to the method of the present invention are similar in morphology to embryonic stem cells and the iPS used for protein extraction to the extent that they cannot be distinguished from each other (FIG. 1D). Also, the pluripotent stem cells reprogrammed according to the method were observed to be positive to alkaline phosphatase staining (FIG. 1E). The feeder cells appeared staining negative (gray).

Example 2

Gene and Protein Characterization of Customized Pluripotent Stem Cells (1) Gene Expression Analysis After being detached by treatment with trypsin-EDTA, the cells of Example 1 were incubated for 30 min in a culture dish in an incubator. While the feeder cells adhered again to the dish, the undifferentiated pluripotent stem cells remained floating and harvested. Total RNA was isolated using a TRIzol reagent (Invitrogen). RT-PCR was performed to produce cDNA, followed by PCR with primers specific for Nanog, Oct4, Sox-2, E-Ras, Klf-4, c-Myc, and a control gene GAPDH (glyceraldehyde 3-phosphate dehydrogenase). All of the genes Nanog, Oct4, Sox-2 and E-Ras are characteristic of embryonic stem cells while Klf-4 and c-Myc are non-specific genes found in both embryonic stem cells and adult somatic cells. The PCR products were analyzed by agarose gel electrophoresis. The results are given in FIG. 2A.

As seen in FIG. 2A, Nanog, Oct4, Sox-2, and E-Ras, which are hallmark genes of embryonic stem cells, were expressed in the pluripotent stem cells (FVBsFB-iPSe1 and C57sFB-iPSe2) reprogrammed according to the method of the present invention, but not in the feeder cells (STO) and the pre-reprogrammed adult somatic cells (C57sFB and FVBsFB). In FIG. 2A, C57 mES and FVBsFB-iPS stand respectively for C57 mouse embryonic stem cells, and iPS cells induced with an extract of the mouse embryonic stem cells. Also, the non-specific genes Klf-4 and c-Myc were expressed in both the cells before and after the reprogramming process.

(2) Protein Expression Analysis

The pluripotent stem cells reprogrammed according to the method of the present invention, C57sFB-iPSe2, were examined to determine whether they expressed SSEA1 (stage-specific embryonic antigen-1) and Oct4, which are characteristic of embryonic stem cells. Alkaline phosphatase staining was conducted using a typical kit (Dako). The embryonic stem cell-characteristic proteins SSEA1 and Oct4 were analyzed for protein expression using antibodies thereto. The immunochemical analysis started with fixing the cells with 100% methanol. Then, the cells were washed with PBS and blocked with a 1% BSA solution before they were incubated at 4° C. for 18 hrs with respective primary antibodies to SSEA1 and Oct4 (Santa Cruz Biotechnology). After washing the cells with PBS, a fluorescence-conjugated secondary antibody was applied at room temperature for 1 hr to them. The cells were washed again with PBS and mounted on a confocal microscope with the aid of a mounting solution. Images of the immunochemical analysis are given in FIG. 2B. In the photographs, BF and DAPI stands for bright field and 4',6-diamidino-2-phenylindole. As seen in FIG. 2B, the iPS reprogrammed according to the method of the present invention expressed SSEA1 and Oct4, which are hallmarks of embryonic stem cells.

Example 3

Analysis of Differentiation Potency of Customized Prulipotent Stem Cells

The cells reprogrammed according to the method of the present invention were examined to determine whether they had the same pluripotency as that of embryonic stem cells.

(1) In Vivo Induction of Differentiation

To analyze in vivo potency of the cells reprogrammed by the method of the present invention, the undifferentiated cell colonies grown on the feeder cells were detached by treatment with trypsin-EDTA on Day 18 (D25) after culturing on the feeder cell layer and then incubated for 30 min in a culture dish in an incubator. The undifferentiated pluripotent stem cells which remained still floating were harvested and subcutaneously injected at a dose of $1\times10^7$ cells into severe combined immune deficiency (SCID) mice. Four weeks after the injection, teratoma thus formed was excised, fixed with 4% paraformaldehyde (PFA) and embedded in paraffin. This was sectioned into 10 μm-thick slices which were stained with hematoxylin and eosin.

Figure 3:
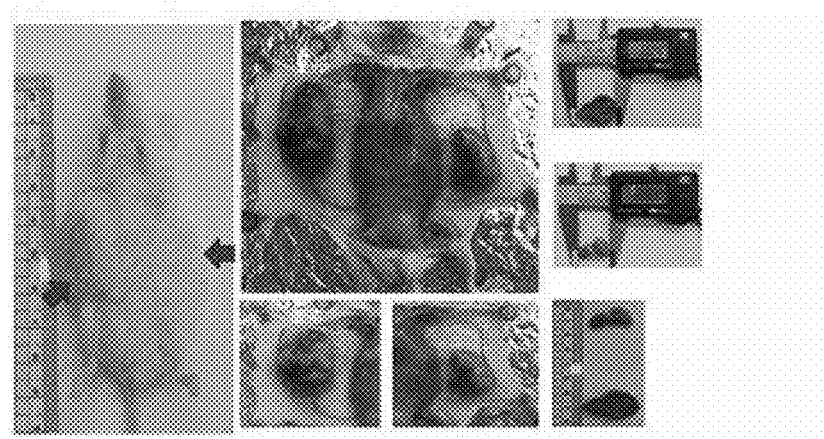
FIG. 3 shows the in vivo pluripotency of the induced pluripotent stem cells according to the present invention.
Figure 3:
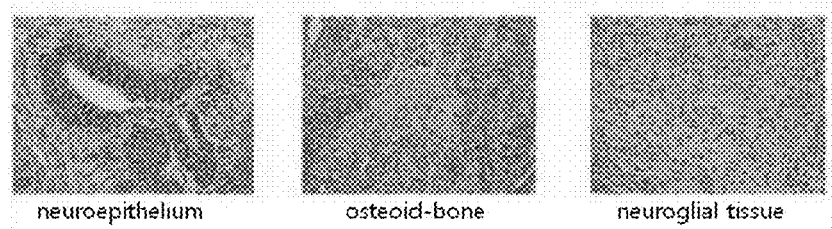
Figure 3:
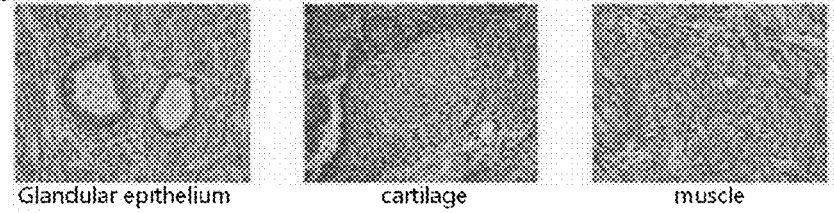
Figure 3:
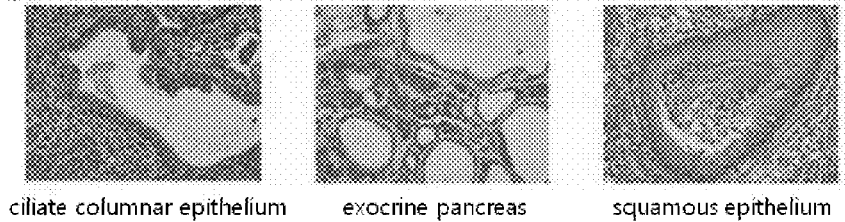

As seen in FIG. 3, teratoma was apparently visualized with the naked eye at the injection site of the iPS reprogrammed by the method of the present invention (FIG. 3A). In greater detail, a histological analysis showed that the teratoma differentiated into the ectoderm including nerve tissues (neuroepithelium, neuroglial tissues, etc. FIG. 3B), the mesoderm including bone tissues and muscle tissues (glandular epithelium, cartilage, muscle, etc. FIG. 3C), and the endoderm including pancreatic tissues (columnar epithelium, exocrine pancreas, squamous epithelium, etc. FIG. 3D).

Accordingly, the cells reprogrammed by the method of the present invention were found to have the same pluripotency to differentiate into the three germ layers including ectoderm, mesoderm and endoderm.

(2) Tetraploid Complementation Assay for In Vivo Pluripontency

To verify the pluripotency of the reprogrammed cells of the present invention in vivo, a tetraploid complementation experiment was performed. In this regard, a tetraploid cell (4n) was produced by taking a mouse embryo (2n) at the two-cell stage and fusing the two cells by electrical manipulation. The tetraploid cells were allowed to be developed into the placenta. In the tetraploid complementation assay, such a tetraploid embryo was combined with the iPS of the present invention. The embryo was then well maintained to develop normally such that the fetus was produced. FIG. 4 shows an embryo at 12.5 days after implantation in the uterine wall of a pseudopregnant female mouse by a tetraploid complementation assay. Therefore, it is apparent that the iPS reprogrammed by the method of the present invention can be developed into an intact individual.

Example 4

Confirmation of Customized Pluripotent Stem Cells by Genotyping

To verify that the reprogrammed pluripotent stem cells of the present invention originated from the adult somatic cells, but not from the protein donor iPS, PCR was performed with specific MIT (microsatellite) markers. The results are given in FIG. 5. In detail, the undifferentiated cell colonies grown on the feeder cells were detached by treatment with trypsin-EDTA on Day 18 (D25) after culturing on the feeder cell layer and washed with cold PBS. After centrifugation, the cell pellet thus formed was resuspended in 200 μL of PBS was transferred to 1.5 mL tubes. With the aid of DNeasy Blood & Tissue Kit and DNeasy mini spin columns, genomic DNA was extracted. PCR was performed using primers for the MIT markers D6Mit102 and D2Mit285, which allow the analysis of genetic polymorphism between individuals, with the genomic DNA serving as a template. The PCR products were run on 2% agarose gel in the presence of an electric field and visualized by staining with EtBr.

As seen in FIG. 5, no genotype coincidence was found between the C57 mouse-derived adult somatic cells (C57 cFB; C57 BL6 mouse-derived cardiac fibroblast) and the FVB mouse-derived adult somatic cells (FVB sFB; FVB mouse-derived skin fibroblast) while the C57 mouse-derived embryonic stem cells (C57 mES) showed the same genotype as the C57 mouse-derived somatic cells. In addition, the pluripotent stem cells (FVBsFB-iPS) reprogrammed by infusing the FVB mouse-derived somatic cells (FVBsFB) with an extract of the C57 mouse embryonic stem cell (C57 mES) was incident in genotype with the FVB mouse-derived adult somatic cells (FVBsFB), but not with the extract donor (C57 mES). These results indicate that the reprogrammed pluripotent stem cells (FVBsFB-iPS) are of customized pluripotent stem cells which originated from the extract-infused adult somatic cells (FVBsFB).

Further, the reprogrammed pluripotent stem cells (C57sFB-iPSe2) of the present invention, prepared by infusing the C57 mouse-derived fibroblast with the FVB mouse-derived iPS protein extract was coincident in genotype with the C57 mouse-derived somatic cells (C57 cFB), but not with the extract donor FVB mouse-derived adult somatic cells ((FVB sFB) (FIG. 5).

It is apparent from the data that the reprogrammed stem cells of the present invention are immunocompatible, customized pluripotent stem cells which have the same genotype as the adult somatic cells from which they originate.

Example 5

Comparison of iPS Production Yield

With regard to iPS production yield, a comparison was made between an embryonic stem cell protein extract and an iPS protein extract. Specifically, proteins were extracted from C57 mouse embryonic stem cells (C57 mES), and from iPS (FVBsFB-iPS) prepared by infusing an extract of C57 mES, according to the method of Example 1(1). These extracts were infused into adult somatic cells (CC57 BL6 mouse fibroblast, C57sFB) according to the methods of Examples 1(2) and 1(3). The adult somatic cells, whether infused with the embryonic stem cell extract or the iPS extract, were cultured at 37° C. in the same embryonic stem cell medium as in Example 1(3) in a 5% $CO_2$ incubator. The medium was changed with a fresh one for the first time after incubation for two days, and then every day. On Day 5 of culture, the cells were transferred onto a mitomycin C (MMC)-treated feeder cell layer and divided into two groups at a ratio of 1:2 per dish. The medium was newly changed every day, with passage onto a new feeder cell layer at regular intervals of five days.

First, as for the time of colony formation, customized pluripotent stem cells were obtained on Day 14 of culture on average when the mouse embryonic stem cells (C57 mES) were used Occasionally, it took 30 days (on Day 37 of culture) for the cells to start to form colonies. On the other hand, the use of the iPS (FVBsFB-iPS) extract allowed colonies to be visualized before Day 14 of culture (on Day 9 after transferring on feeder cells) (FIG. 6B).

Turning to the number of colonies during culture, when the mouse embryonic stem cell (C57 mES) extract was used, small colonies started to form on Day 7 after the cells were transferred onto the feeder STO cells. On 25th day (D32), 10~20 more mature, relatively large colonies were observed. Only after 60 days of culture (D67), as many as 200 colonies were formed. On the other hand, the use of the iPS (FVBsFB-iPS) extract allowed the formation of about 4~5 small colonies on 4th day (D11), 20~30 more mature, relatively large colonies on 7th day (D14), more than 200 colonies on 10th day (D17) and innumerable mature colonies on the 18th day (D25). Therefore, the formation of 200 or more colonies required about 10 days after transfer onto STO cells upon the use of the iPS extract while it took about 60 days when the embryonic stem cell extract was used.

Figure 7:
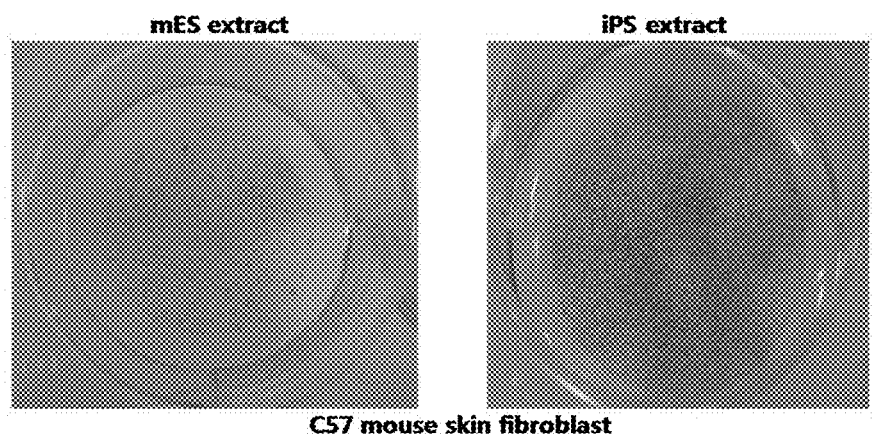
FIG. 7 shows the comparison of iPS production yield between an embryonic stem cell extract and an iPS extract (b) in photographs of the cells on day 31 of culture after alkaline phosphatase staining (a and b) and in a graph presenting colony numbers (c).
Figure 7:
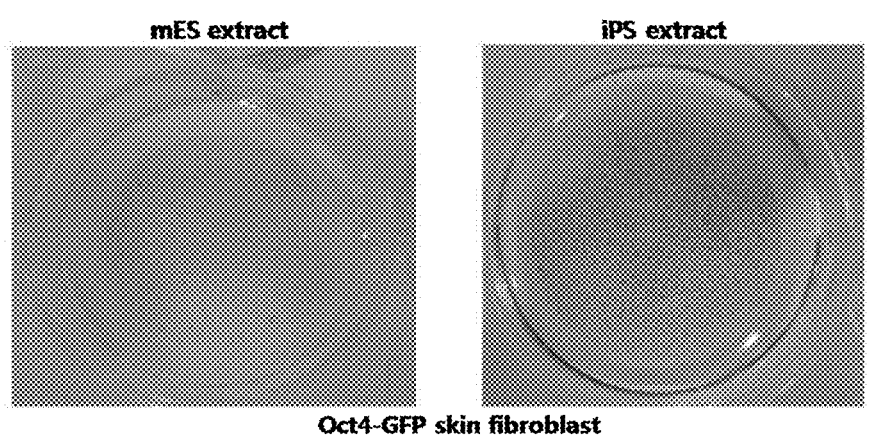
Figure 7:
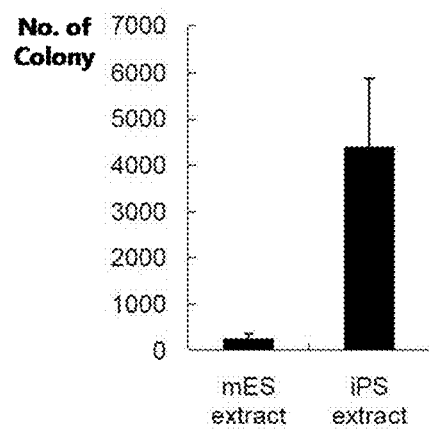

FIG. 7A shows the alkaline phosphatase staining pattern of the cells on the 31st day of culture. As seen in the photographs, the c57 mouse fibroblast cells treated with the iPS extract were significantly higher positive to alkaline phosphatase staining than those treated with the embryonic stem cell extract. Oct4-GFP transgenic mouse skin fibroblast cells were also reprogrammed to dedifferentiate into pluripotent stem cells at significantly higher yield upon the use of the iPS extract than the embryonic stem cell extract, as shown in FIG. 7B. As is apparent from the data of FIG. 7C in which the average numbers of colonies formed with the mES extract and the iPS extract are graphed with regard to the results of FIGS. 7A and 7B, the iPS extract can induce adult somatic cells to dedifferentiate into pluripotent cells at significantly higher yield than can the embryonic stem cell extract.

In addition, to analyze the underlying mechanism with regard to the higher induction efficiency of the iPS extract than the embryonic stem cell extract, telomere lengths were compared between the embryonic stem cells and iPS.

Figure 8:
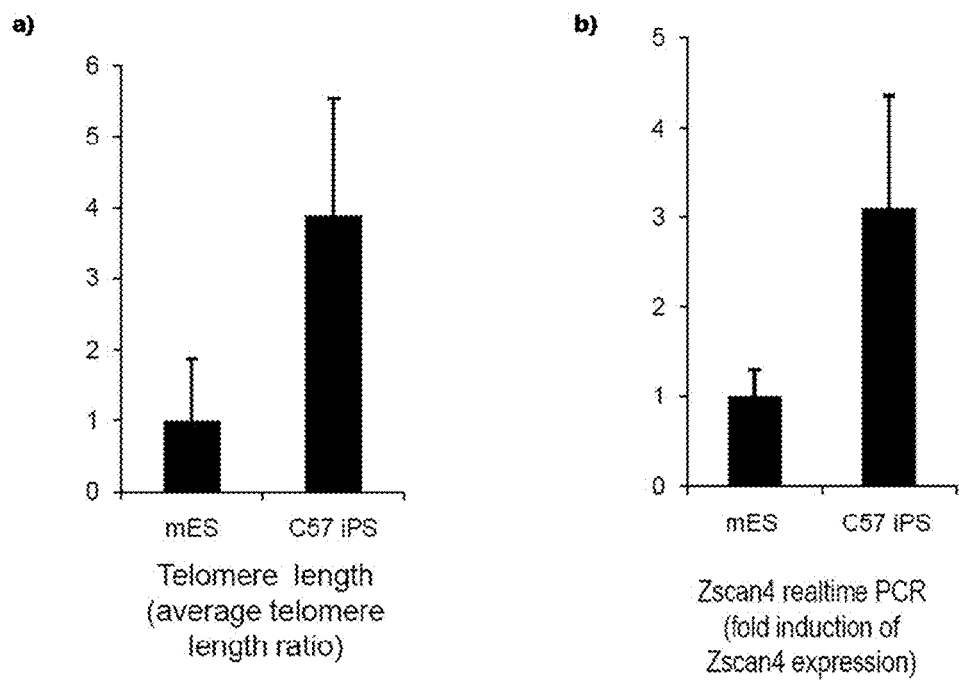
FIG. 8 are of graphs showing the telomere lengths of embryonic stem cells & iPS (a) and the expression levels of Zscan4 compared therebetween (b).

In detail, RNA isolated from the embryonic stem cells and C57 iPS were subjected to real-time PCR and the results are given in FIG. 8A. As seen in the graph of FIG. 8A, the telomere of C57 iPS was observed to be four time as long as that of mES. The longer the telomere, the younger and fresher cells. From the result, thus, iPS was considered to be younger and fresher and be significantly higher in pluripotency than mEs.

On the basis of the report that the telomere length of stem cells is regulated by Zscan 4 through recombination, RNA isolated from mEs and C57 iPS was subjected to PCR using primers for Zscan4. The relative expression levels are shown in FIG. 8B. As seen in FIG. 8B, the Zscan4 gene was expressed at a three-fold higher level in iPS than mEs.

These results indicate that iPS expresses the Zscan4 gene at a higher level and has longer telomeres than embryonic stem cells, and an iPS extract can reprogram adult somatic cells to dedifferentiate into pluripotent cells at significantly higher yield than can embryonic stem cells.

Consequently, the iPS extract according to the present invention allows customized pluripotent stem cells to be readily produced in a great amount within a short period of time, and is expected to greatly contribute to the commercialization of cell therapy.

INDUSTRIAL APPLICABILITY

As described hitherto, the method of the present invention can induce pluripotent stem cells very easily and at significantly higher yield than can conventional methods. The pluripotent stem cells reprogrammed according to the method of the present invention can be commercialized for use as an immunocompatible cell therapeutics customized for individuals. Accordingly the present invention can greatly contribute the treatment of various incurable diseases such as cardiovascular diseases, nerve system diseases, diabetes, etc. Further, the method can be used in the production of cloned animals while maintaining a high level of safety and efficiency.

It is understood to a person skilled in the art that the above description of the present invention is susceptible to various modifications, changes and adaptations, and the same are intended to be comprehended within the meaning and range of equivalents of the appended claims. Therefore, the embodiments and attached drawings disclosed in the present invention are not intended to limit the technical spirit of the present invention, but are intended to describe the invention. The technical spirit of the present invention is not limited to such embodiments and drawings.

What is claimed is:

1. A method for producing a pluripotent stem cell, comprising:
   a) extracting proteins from induced pluripotent stem (iPS) cells;

b) introducing the protein extract obtained from step (a) into adult somatic cells; and
c) culturing the adult somatic cells of step (b) in embryonic stem cell medium to induce pluripotent stem cells having the same pluripotency as that of embryonic stem cells.

2. The method according to claim 1, wherein the protein extract ranges in concentration from 10 to 50 mg/ml.

3. The method according to claim 2, wherein the protein extract ranges in concentration from 20 to 30 mg/ml.

4. The method according to claim 1, further comprising treating the adult somatic cells with a membrane permease before the introduction of the protein extract.

5. The method according to claim 1, wherein the embryonic stem cell medium is a DMEM (Dulbecco's Modified Eagle Medium) supplemented with 10% FBS (Fetal Bovine Serum), 0.1 mM MEM (Minimum Essential Medium) non-essential amino acids, 0.1 mM β-mercaptoethanol, 100 U/ml penicillin, 100 μg/ml streptomycin, and 20 ng/ml leukemia inhibitory factor.

6. The method according to claim 1, wherein step c) further comprises transferring and culturing the adult somatic cells on a feeder cell layer.

7. The method according to claim 6, wherein the feeder cell layer comprises STO cells.

8. The method according to claim 6, wherein the adult somatic cells are transferred onto the feeder cell layer on day 7 after culturing.

9. A method for producing a pluripotent stem cell, comprising:
a) extracting proteins from induced pluripotent stem cells the concentration of the proteins being 20-30 mg/ml after extraction;
b) treating adult somatic cells with a membrane permease;
c) introducing the protein extract of a) into the adult somatic cells of b);
d) culturing the adult somatic cells of c) in an embryonic stem cell medium; and
e) transferring and culturing the adult somatic cells of d) on a feeder cell layer 7 days after the above culturing step.

10. The method according to claim 9, wherein the adult somatic cells of e) are cultured for an additional 14 days after transfer onto the feeder cell layer.

* * * * *